US006995293B2

(12) United States Patent
Bohnen et al.

(10) Patent No.: US 6,995,293 B2
(45) Date of Patent: Feb. 7, 2006

(54) METHOD FOR THE PRODUCTION OF ALDEHYDES

(75) Inventors: Hans Bohnen, Moers (DE); Jurgen Herwig, Hunxe (DE); Dietmar Hoff, Wuppertal (DE); Peter Wasserscheid, Cologne (DE); Roy van Hal, Schinveld (NL)

(73) Assignee: Celanese Chemicals Europe GmbH, (DE)

( * ) Notice: Subject to any disclaimer, the term of this patent is extended or adjusted under 35 U.S.C. 154(b) by 71 days.

(21) Appl. No.: 10/654,494

(22) Filed: Sep. 3, 2003

(65) Prior Publication Data

US 2005/0085671 A1    Apr. 21, 2005

(30) Foreign Application Priority Data

Sep. 19, 2002  (DE)  ............................... 102 43 446

(51) Int. Cl.
 *C07C 45/49*  (2006.01)
 *C07C 45/50*  (2006.01)
(52) U.S. Cl. ...................... 568/429; 568/451; 568/454
(58) Field of Classification Search ................ 568/429, 568/451, 454
 See application file for complete search history.

(56) References Cited

U.S. PATENT DOCUMENTS

| 4,879,418 A | * | 11/1989 | Bach et al. .................. 568/454 |
| 6,114,272 A | * | 9/2000 | Bahrmann .................. 502/164 |
| 6,410,799 B1 | * | 6/2002 | Favre et al. ................. 568/420 |
| 6,472,565 B1 | * | 10/2002 | Bahrmann et al. .......... 568/454 |
| 2002/0115892 A1 | | 8/2002 | Mackewitz | |

FOREIGN PATENT DOCUMENTS

| DE | 26 27 354 | 12/1976 |
| EP | 0 776 880 A1 | 6/1997 |
| EP | 1 182 197 A1 | 2/2002 |
| EP | 1 241 156 A1 | 9/2002 |
| WO | WO 98/30526 PCT | 7/1998 |
| WO | WO 03/022812 PCT | 3/2003 |
| WO | WO 03/074494 PCT | 9/2003 |

OTHER PUBLICATIONS

W.P. Mul, New, Highly . . . Diphosphines, Advanced Synthesis & Catalysts, 2002 pp. 293-298.
P. Wasserscheid, 1-n-Butyl . . . Ionic Liquid, Green Chemistry, 2002, 4 pp. 400-404.
P. Wasserscheid, Ionic . . . Ubergangsmetallkatalyse, Angew Chem., 2000 112, pp. 3927-3945.

* cited by examiner

*Primary Examiner*—Sikarl A. Witherspoon
(74) *Attorney, Agent, or Firm*—Charles A. Muserlian

(57) ABSTRACT

The present invention relates to a hydroformylation method by conversion of olefins or olefinically unsaturated compounds in the presence of at least one rhodium compound and in the presence of sulfonated arylphosphines in ionic liquids, which are based on a quaternary singly-charged ammonium ion or the equivalent of a multiply charged ammonium ion and organic sulfonates or sulfates.

19 Claims, No Drawings

METHOD FOR THE PRODUCTION OF ALDEHYDES

The present invention relates to a method for the production of aldehydes by conversion of olefins or olefinically unsaturated compounds with hydrogen and carbon monoxide (hydroformylation) in the presence of rhodium or rhodium compounds, sulfonated aryl phosphines and a non-aqueous ionic liquid of the general formula $(Q^e)_a A^{a'''}$. In this formula, $Q^e$ represents a singly charged ammonium cation, possibly, if appropriate substituted by organic radicals, or the equivalent of a multiply charged ammonium cation, possibly substituted by organic radicals, and $A^{a'''}$ represents an organic sulfonate or organic sulfate. a is an integer at least equal to 1, and describes the charge of the anion or the number of cations with charge +1 in the compounds corresponding to the general formula.

Aldehydes are of great economic significance as valuable intermediate products in industrial chemistry. From them can be prepared, for example, alcohols, carboxylic acids and amines, which, in turn, are employed as starting materials for the production of important end products.

Hydroformylation is among the most widely practiced industrial processes. The reaction is catalyzed by hydrido metal carbonyls preferably those of metals of group VIII of the periodic table of the elements. While cobalt was initially exclusively applied industrially as the catalyst metal, current processes employing rhodium as the catalyst metal, are gaining increasingly in importance.

The preparation of aldehydes by hydroformylation of olefins can take place in a single organic phase. The catalyst, for example a rhodium/triphenylphosphine complex, is dissolved in the reaction mixture formed of starting material and reaction product. In addition, an organic solvent, for example toluene, xylene or tetrahydrofuran, can be introduced.

The separation of the reaction products and the recovery of the catalysts dissolved homogeneously in the reaction product present problems in this process. For this purpose the conversion product is in general distilled off from the reaction mixture. But, due to the thermal sensitivity of the formed aldehydes and the therein entailed formation of byproducts at the expense of aldehyde yield, this path can in practice only be followed in the hydroformylation of lower olefins, i.e. olefins with up to approximately 5 carbon atoms in the molecule. In addition, the-thermal loading of the material being distilled can lead to considerable losses of catalyst through the decomposition of catalytically active complexes.

These shortcomings can be avoided if the hydroformylation reaction is carried out in a two-phase system. Such a process is described for example in DE 26 27 354. This process is characterized by the presence of an organic phase, which contains the starting olefins and the reaction product, and an aqueous phase, in which the catalyst is dissolved. Water-soluble rhodium complexes, which contain water-soluble phosphines as ligands, are employed as catalysts. In particular, these phosphines are triarylphosphines, trialkylphosphines and arylated or alkylated diphosphines, whose organic radicals are substituted by sulfonic acid groups or carboxyl groups. Their preparation is disclosed, for example, in DE 26 27 354.

The bi-phasic hydroformylation process carried out in the presence of an aqueous catalyst-containing phase is useful especially in the hydroformylation of lower olefins, in particular with ethylene and propylene. If, in contrast, higher olefins, such as hexene, octene or decene are employed, the conversion decreases markedly. The reduction of the conversion is most likely due to the decreased solubility of higher olefins in water, since it is assumed that the reagents react in the aqueous phase. This hypothesis is supported by the fact that the olefin conversion is markedly increased if a phase transfer reagent (solubilizer) is added to the aqueous solution of catalyst. According to EP-B-0 562 451 cationic solubilizers of the general formula $[A-N(R^1R^2R^3)]^+E''$ have been found especially useful, in which A represents a -straight-chain or branched alkyl radical with 6 to 25 carbon atoms, $R^1$, $R^2$, $R^3$ are identical or different and represent straight-chain or branched alkyl radicals with 1 to 4 carbon atoms, and E'' represents an anion, in particular sulfate, tetrafluoroborate, acetate, methosulfate, benzenesulfonate, alkylbenzenesulfonate, toluenesulfonate, lactate or citrate.

Apart from the adequate solubility of the olefin in the aqueous phase, for the biphase performance of the hydroformylation processes in the presence of an aqueous catalyst-containing phase, sufficient stability of the olefin to be converted in water is necessary. For that reason water-sensitive olefins, such as for example acrylic esters or unsaturated acetals, cannot be successfully employed according to this process.

So-called ionic liquids have recently received attention as solvents for the catalyst. Ionic liquids are low-melting salts, which are liquid below a temperature of 100° C. and which have practically no vapor pressure. Ionic liquids can serve as solvents for catalytically active transition metal complexes and ligands present in excess, and they frequently form a separate phase from the organic product phase. The use of ionic liquids, therefore, also permits conducting bi-phasic reactions in the absence of water and, after the reaction has gone to completion, the organic product phase and the ionic phase containing the dissolved catalytic transition metal complex, can be separated in simple manner by means of phase separation.

By means of ionic liquids bi-phasic processes can be carried out under non-aqueous conditions. Properties, production and application of ionic liquids are extensively discussed in the overview articles in Angew. Chem. 2000, 112, 3926–3945 and Chem. Commun., 2001, 2399–2409.

CHEMTECH, September 1995, pp. 26 to 30 describes catalytic reactions in a nonaqueous two-phase system. According to this description, nonaqueous ionic liquids, which are already liquid at room temperature, for example a mixture of 1,3-dialkylimidazolium chloride, preferably 1-n-butyl-3-methylimidazolium chloride (abbreviated $[BMI]^+[Cl]''$)/and aluminum chloride and/or ethylaluminum dichloride are used as solvent for the catalyst. As examples of reactions carried out with such catalyst solutions are listed the olefin dimerization in the presence of nickel complex compounds, for example propene dimerization to isomeric hexenes or the butene dimerization to iso-octenes. In these conversions, the reaction product accumulates as the upper phase, while the catalyst-containing nonaqueous ionic liquid forms the lower phase and can be separated by simple phase separation. The solution of the catalyst in the nonaqueous ionic liquid can be introduced again into the process.

Am. Chem. Soc, Div. Pet. Chem. 1992, 37, pp. 780 to 785 reports use of a nonaqueous ionic liquid, comprised of $[BMI]^+[Cl]''$ and aluminum chloride, as solvent, in that after the addition of ethyl aluminum chloride and $NiCl_2(PR_3)_2$, where R represents isopropyl, the dimerization of propene takes place.

The use of low-melting phosphonium salts, for example tetrabutylphosphonium bromide, as the solvent in hydroformylation reactions is described in the Journal of Molecular Catalysis, 47 (1988) pp. 99 to 116. Described is the hydroformylation of olefins, for example octene-1, with ruthenium carbonyl complexes in the presence of nitrogen or phosphorus-containing ligands, for example of 2,2'-dipyridine or 1,2-bis(diphenylphosphino)ethane, at temperatures of 120 to 180° C. leads to a mixture of n-nonanol and n-nonanal. This process yields a reaction mixture with an n-nonanol proportion of up to 69% wt %, relative to the reaction mixture. The isolation of the desired n-nonanal therefore requires considerable distillation expenditure.

European patent application EP-A-0 776 880 discloses the hydroformylation of olefins in the presence of quaternary ammonium and/or phosphonium salts as solvents for the catalyst. Preferred are salts containing [BMI]$^+$ as the cation.

Salts of quaternary diamines, in which-the cation has the general formula

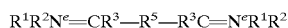

$$R^1R^2N^e=CR^3-R^5-R^3C=N^eR^1R^2$$

where $R^1$, $R^2$, $R^3$ are identical or different and represent hydrogen or a hydrocarbon radical with 1 to 12 carbon atoms and $R^5$ an alkylene radical, for example methylene (—CH$_2$—), ethylene (—CH$_2$—CH$_2$—), propylene (—CH$_2$—CH$_2$—CH$_2$—) or a phenylene radical, are used as solvents for hydroformylation catalysts. Suitable anions are for example hexafluorophosphate, hexafluoroantimonate, tetrachloroaluminate or tetrafluoroborate. These quaternary ammonium and/or phosphonium salts are already liquid below 90° C, preferably below 85° C. and particularly preferable below 50° C.

The hydroformylation catalyst dissolved in said solvents contains as the active metal cobalt, rhodium, iridium, ruthenium, paladium or platinum and as ligands a tertiary phosphine or tertiary sulfonated phosphine, a tertiary arsane, tertiary stibane or a phosphite. The molar ratio of ligand to metal is 9.5.

The catalytically active metals are employed as compounds, rhodium, for example, in the form of rhodium acetylacetonatedicarbonyl or rhodium carbonyl Rh$_6$(CO)$_{16}$. Under the reaction conditions the hydroformylation catalyst is formed, it is – . . . especially preferred if the hydroformylation reaction is carried out between 30 and 90° C.

According to Angew. Chem. 1995, 107 No. 23/24, pp. 2941 to 2943 hydroformylation reactions can also be carried out using 1,3 dialkylimidazolium salts liquid at ambient temperature as the catalyst-containing solvent, which does not mix with the organic reaction mixture. For this purpose, rhodium dicarbonylacetylacetonate is added as a catalyst precursor to a solution of triphenylphosphine in [BMI]$^e$ [PF$_6$]$^e$. The molar ratio of phosphorus (III) to rhodium can vary from 3 to 10." The catalyst is preformed with synthesis gas (ratio of volume of hydrogen to carbon monoxide equals 1:1). Subsequently, n-pentene-1 is converted by use of synthesis gas of equal composition at a temperature of 80° C. In this case the organic product phase can also be separated in simple manner by decantation from the catalyst-containing, nonaqueous ionic liquid.

Apart from discharge of the phosphine ligand, the transfer of the catalytically active metal from the nonaqueous ionic liquid into the organic phase is of disadvantage in the known processes. According to prior art, this disadvantage can be circumvented if, in place of neutral ligands, such as triphenylphosphine, charged ligands, for example mono- or tri-sulfonated triphenylphosphine are used, since it can be expected that charged ligands will increase the solubility of the catalytically active metal compounds in the nonaqueous ionic liquid. While it was possible to reduce the discharge of the catalytically active metal by using charged ligands, however, the aldehyde yields decreased simultaneously to only 16 to 33% (Angew. Chem. 1995, 107 No. 23/24 pp. 2941 to 2943, EP-A-0 776 880).

In the variant known from Chem. Commun. 2001, 451–452 the polarity of the ligands is increased by introducing the positively charged guanidinium group to the aromatic 'radical The ionic liquids known so far are based largely on low-melting salts with ammonium or phosphonium cations and complex anions containing halogens, such as fluorine or chlorine.

Due to the corrosive behavior of halogen-containing melts toward reaction vessels fabricated of metallic materials, application of such salt melts on an industrial scale presents the danger of intensified loading of the metallic reactor vessels.

In addition, the disposal of the accumulated halogen-containing salt melt after the catalyst system is exhausted is especially expensive and elaborate.

The problem therefore arose of developing a process for hydroformylation of olefins or olefinically unsaturated compounds in the presence of a catalytically active metal and a nonaqueous ionic liquid, which avoids the described disadvantages.

The invention comprises a process for the production of aldehydes by conversion of monoolefins, conjugated and nonconjugated polyolefins, cycloolefins or derivatives of these classes of compounds with carbon monoxide and hydrogen at temperatures of 20 to 150° C. and pressures of 0.1 to 20 MPa in the presence of a nonaqueous ionic liquid having the general formula $(Q^e)_aA^{a''}$ and at least one rhodium compound and at least one sulfonated arylphosphine. It is characterized thereby that $Q^e$ is a singly charged ammonium cation, which may be substituted by organic radicals, or the equivalent of a multiply charged ammonium cation, which may be substituted by organic radicals, and $A^{a''}$ represents an organic sulfonate or organic sulfate having the general formula

$$R^1\{SO_3-\}_a \text{ or } R^2\{OSO_3-\}a \tag{1}$$

where $R^1$ and $R^2$ represents a straight-chain or branched alkyl radical with 1 to 20 carbon atoms, an alkylaryl radical with 7 to 20 carbon atoms, an aryl radical with 6 to 14 carbon atoms, a cycloalkyl radical with 3 to 7 carbon atoms or an aralkyl radical with 7 to 20 carbon atoms; or $R^1$ represents a radical having the general formula

$$R^3-O\{(CH_2)_nO\}_m \tag{1a}$$

in which $R^3$ represents a straight-chain or branched alkyl radical with 1 to 20 carbon atoms, an alkylaryl radical with 7 to 20 carbon atoms, an aryl radical with 6 to 14 carbon atoms, a cycloalkyl radical with 3 to 7 carbon atoms, or an aralkyl radical with 7 to 20 carbon atoms, n is an ingeter from 2 to 12 and m assumes integer values from 1 to 100; and a is an integer and represents the number of the sulfone or sulfate radicals bound to the organic radical and is at least equal to 1.

It was surprisingly found that rhodium compounds dissolved in the nonaqueous ionic liquids applied according to the invention are highly suitable for the hydroformylation of olefins or olefinically unsaturated compounds.

Especially useful in the hydroformylation process according to the invention have been such ionic liquids of the general formula (1), in which $R^1$ or $R^2$ repreent a straight-chain or branched alkyl radical with 1 to 12 carbon atoms, an alkylaryl radical with 7 to 12 carbon atoms, an aryl radical with 6 to 10 carbon atoms, a cycloalkyl radical with 5 to 7 carbon atoms or an aralkyl radical with 7 to 12 carbon atoms, $R^3$ represents a straight-chain or branched alkyl radical with 1 to 12 carbon atoms, an alkylaryl radical with 7 to 12 carbon atoms, an aryl radical with 6 to 10 carbon atoms, a cycloalkyl radical with 5 to 7 carbon atoms or an aralkyl radical with 7 to 12 carbon atoms, n equals 2, 3 or 4, m is an integer between 1 and 50 and a equals 1 or 2.

In particular the use of the anions octylsulfate and ttisylate has been found to be suitable.

Ionic liquids based on sulfone- or sulfate-containing anions, in comparison to the known ionic liquids, which contain complex anions with halogens as components, such as for example hexafluorophosphate or tetrafluoroborate anion, are distinguished by their weakened corrosive effect on metallic equipment parts. As a consequence of this lower corrosive loading the susceptibility to repairs of the employed apparatus parts decreases, which has an advantageous effect on the economy of the hydroformylation process. In addition, when using the ionic liquids of the general formula (1), hydroformylation reactions can be carried out in reaction vessels, which can be fabricated of materials having lower corrosion resistance. The use of such cost-effective material for the reaction vessels has an especially high economic value, since this lowers the investment costs.

It has moreover surprisingly been found that when using the anions of the general formula (1) in the ionic liquid in hydroformylation processes, higher conversion and selectivity values to the straight-chain aldehydes can be attained in comparison to hydroformylation processes, which are carried out in conventional ionic liquids using halogen-containing complex anions. Without wishing to offer a theoretical interpretation for this surprising effect, it can be assumed that the organic radicals bound in the anions of general formula (1) increase the solubility of the olefinically unsaturated compounds in the ionic liquid.

The ionic liquids employed in the hydroformylation process according to the invention contain as cations $Q^e$ especially organic radical-substituted ammonium ions, namely ammonium ions, which are derived from mono- or diamines. The ammonium ions of monoamines correspond to the general formulas (2) and (3)

  (2)

  (3)

where $R^4$, $R^5$, $R^6$ and $R^7$ are identical or different and are hydrogen, in particular with the provision that at least one $R^4$, $R^5$, $R^6$, $R^7$ is not hydrogen, or represents a linear or branched, aliphatic hydrocarbon radical with 1 to 20 carbon atoms, a cycloaliphatic or aromatic hydrocarbon radical with 6 to 20 carbon atoms or an alkoxy radical with 1 to 10 carbon atoms. Examples of such radicals are alkyl, alkenyl, cycloalkyl, aryl, alkylaryl or aralkyl radicals.

As cations of the ionic liquid are further possible ions derived from saturated or unsaturated cyclic compounds as well as from aromatic compounds each with a tridentate N atom in the 4 to 10, preferably 5 to 6-membered heterocyclic ring. Such cations can be represented in simplified form (i.e. without specification of precise position and number of double bonds in the molecule) by the following general formulas (4) and (5).

 (4)

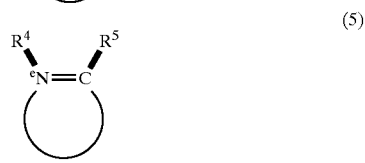 (5)

—$R^4$ and $R^5$ have the above provided significance. Examples of cyclic amines of said type are pyrrolidine, dihydropyrrole, pyrrole/indole, carbazole, piperidine, the isomeric picolines and lutidines, quinoline and i-quinoline.

Preferred cations are based on aliphatic, cycloaliphatic or aromatic diamines. They follow the general formulas (6) and (7)

 (6)

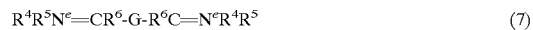 (7)

in which $R^4$, $R^5$, $R^6$, $R^7$, $R^8$ and $R^9$ are identical or different and represent hydrogen, a linear or branched aliphatic hydrocarbon radical with 1 to 20 carbon atoms, a cycloaliphatic or aromatic hydrocarbon radical with 6 to 30 carbon atoms, an alkylaryl or aralkyl radical with 7 to 40 carbon atoms or an alkoxy radical with 1 to 10 carbon atoms. G represents an alkylene radical (—$CHR^{10}$—)$_d$, where $R^{10}$ represents hydrogen or a hydrocarbon radical with 1 to 5 carbon atoms and d is an integer from 1 to 8, preferably 2 to 6, an arylene radical with 6 to 30 carbon atoms or an alkylenearyl radical with 7 to 40 carbon atoms. Examples of the hydrocarbon radicals denoted by $R^4$, $R^5$, $R^6$, $R^7$ $R^8$ and $R^9$ are alkyl, alkenyl, cycloalkyl, aryl, alkylaryl or aralkyl radicals, such as methyl, ethyl, propyl, i-propyl, butyl, sec. butyl, t-butyl, amyl, methylene, ethylidene, phenyl, and/or benzyl. For example, $R^{10}$ is described by methyl, ethyl, n-propyl, i-propyl radical and the isomeric butyl radicals. Examples of G are the radicals methylene, ethylene, propylene, butylene, 1,4-phenylene, 1,4-toluylene, 1,4-xylylene, 1^'-biphenyl-^'-diyl, 1,4-naphthylene, 1,1-binaphthy 1-2,2'-diyl.

Further preferred cations of the nonaqueous ionic liquids according to the invention are diamines based on 1-amino-3-dialkylaminopropanes having the general formula (8)

 (8)

in which $R^{11}$ and $R^{12}$ are identical or different linear or branched alkyl radicals with 4 to 20 carbon atoms and represent for example n-butyl, n-pentyl, n-hexyl, n-heptyl, i-heptyl, n-octyl, i-octyl, n-nonyl, i-nonyl, n-decyl, i-decyl, n-undecyl, i-undecyl, rill dodecyl or i-dodecyl.

Further advantageous cations of the nonaqueous ionic liquids according to the invention are based on the following amines: 1-amino-3-(di-n-heptyl)-aminopropane, 1-amino-3-(di-i-heptyl)-aminopropane, 1-amino-3-(di-n-octyl)-aminopropane, 1-amino-3-(di-i-octyl)-aminopropane, 1-amino-3-(di-n-nonyl)-aminopropane, 1-amino-3-(di-i-nonyl)-aminopropane, 1-amino-3-(di-n-undecyl)-aminopropane, 1-amino-3-di-i-undecyl)-aminopropane, 1-amino-3-(di-n-dodecyl)-aminopropane or 1-amino-3-(di-i-dodecyl)-aminopropane.

The above described 1-amino-3-dialkylaminopropanes are readily accessible from N,N-(dialkyl)amines and acrylonitrile (cf. Ullmann's Encyclopedia of Industrial Chemistry, Vol. A2, 1985).

Lastly, among the diamines that yield especially suitable cations for the ionic liquids, are also heterocyclic compounds. Among them are saturated or unsaturated as well as aromatic compounds each with two tridentate N atoms in the 4 to 10, preferably 5 or 6-membered heterocyclic ring. These compounds can be substituted at the carbon atoms as well as also at the nitrogen atoms, preferably by alkyl radicals with 1 to 10 carbon atoms and by phenyl radicals. They may moreover be fused by benzene rings and/or cyclohexane rings substituted as desired to yield polycyclic structures. Examples of such compounds are pyrazole, 3,5-dimethylpyrazole, imidazole, benzimidazole, dihydropyrazole, pyrazolidine, pyridazine, pyrimidine, pyrazine, 2,3-, 2,5- and 2,6-dimethylpyrazine, cimoline, phthalazine, quinazoline, -phenazine and piperazine. Especially cations derived from imidazole and its alkyl and phenyl derivatives having the general formula (9)

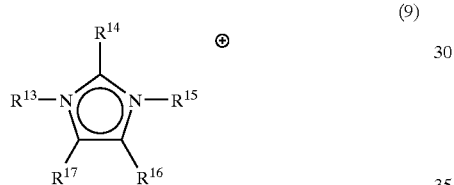

(9)

have been found useful as components of the novel ionic liquids. In this formula $R^{13}$, $R^{14}$, $R^{15}$, $R^{16}$ and $R^{17}$ are identical or different. They represent hydrogen, a $C_1$ to $C_{30}$ alkyl radical, a $C_6$ to $C_{40}$ aryl radical, a $C_7$ to $C_{40}$ alkylaryl radical or an $SiR_3^{18}$ radical, in which $R^{18}$ represents a $C_1$ to $C_{30}$ alkyl radical or a $C_6$ to $C_{40}$ aryl radical. Examples of such cations are: 1-ethyl-3-methyl-2,4,5-H-imidazolium, 1-propyl-3-methyl-2,4,5-H-imidazolium, 1-butyl-3-methyl-2,4,5-H-imidazolium, 1-butyl-3-ethyl-2,4,5-H-imidazolium, 1,3,4,5-tetramethyl-2-H-imidazolium, 2,4,5-trimethyl-1,3-H-imidazolium, 1,2,3,4,5-pentamethylimidazolium, 1,2,3,5-tetramethyl-4-H-imidazolium, 1,2,3,4-tetramethyl-5-H-imidazolium, 1,3,4,5-tetraphenyl-2-H-imidazolium, 1,3-dimethyl-4,5-diphenyl-2-H-imidazolium, 1-ethyl-3-isopropyl-2,4,5-H-imidazolium, 1-butyl-3-octanyl-2,4,5-H-imidazolium, 1-propyl-3-octanyl-2,4,5-H-imidazolium, 1-ethyl-3-octanyl-2,4,5-H-imidazolium, 1-methyl-3-octanyl-2,4,5-H-imidazolium, 1,3-diisopropyl-4,5-dimethyl-2-H-imidazolium, 1,4,5-trimethyl-3-trimethylsilyl-2-H-imidazolium, 2-ethyl-4-methyl-1,3,5-H-imidazolium, 1,3-adamantyl-4,5-dimethyl-1-H-imidazolium, 1,2,4,5-tetramethyl-3-H-imidazolium, 1-methyl-2,3,4,5-H-imidazolium, 1,3-dimethyl-2,4,5-H-imidazolium, 2-methyl-4,5-ethyl-1,3-H-imidazolium, 2,4,5-trimethyl-1,3-H-imidazolium, 1-ethyl-2,3,4,5-H-imidazolium, 1,3-diethyl-4,5-dimethyl-2-H-imidazolium, 1,3-diphenyl-4,5-dimethyl-2-H-imidazolium, 1,3-diphenyl-2,4,5-H-imidazolium, 1,3-dimethoxy-4,5-dimethyl-2-H-imidazolium, 1-trimethylsilyl-2,3,5-trimethyl-4-H-imidazolium.

Furthermore, ionic liquids based on sulfone- or sulfate-containing anions of the general formula (1), whose cations are derived from polyamines, have been found very useful. Examples of such polyamines are hexamethylenetetramine and purine as well as their derivatives.

The ionic liquid is not soluble in the organic product phase, which contains the non-reacted olefin, aldehyde and byproducts, for example alcohols. It serves as a solvent for the catalytically active rhodium complex and forms a liquid phase separate from the organic product. As ligands for the rhodium complex are used sulfonated arylphosphines as compounds capable of forming complexes, which dissolve the rhodium complex well in the ionic liquid and as much as possible prevent rhodium transfer into the organic phase.

As sulfonated arylphosphines are suitable for the process according to the invention sulfonated triarylphosphines having the general formula (10)

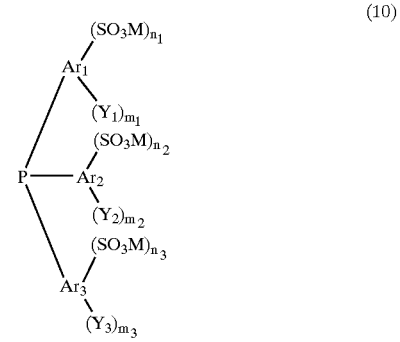

(10)

in which $Ar^1$, $Ar^2$ and $Ar^3$ represent identical or different aryl groups with 6 to 14 carbon atoms, the substituents $Y_1$, $Y_2$ and $Y_3$ represent identical or different straight-chain or branched alkyl or alkoxy radicals with 1 to 4 carbon atoms, chlorine, bromine, the hydroxyl, cyanide or nitro group, further represent the amino group of formula $NR^{18}R^{19}$, in which the substituents $R^{18}$ and $R^{19}$ are identical or different and represent hydrogen, straight-chain or branched alkyl groups with 1 to 4 carbon atoms, in which M represents lithium, sodium, potassium, magnesium/calcium or barium, in which $m_2$, $m_2$ and $m_3$ are identical or different and represent integers from 0 to 5, in which $n_1$, $n_2$ and $n_3$ are identical or different and represent integers from 0 to 3, with at least one of the integers $n_2$, $n_2$ and $n_3$ being equal to or greater than 1.

Among the triarylphosphines are preferably such triarylphosphines, in which the groups $Ar^1$, $Ar^2$, $Ar^3$ are phenyl groups; $Y_1$, $Y_2$ and $Y_3$ represent the methyl, the ethyl group, the methoxy, ethoxy group and/or a chlorine atom; and the cationic radicals M are inorganic cations of sodium, potassium, calcium and barium. Especially suitable are such triarylphosphines, in which $Ar^1$, $Ar^2$, $Ar^3$ each represent a phenyl group, $m_{17}$ $m_2$, $m_3$ are equal to 0, $n_1$, $n_2$ and $n_3$ are equal to 0 or 1, and $n$ $n_2+n_3$ together equal 1 to 3 and in which the sulfonate groups are in the meta position.

A mixture suitable for carrying out the hydroformylation process according to the invention of (sulfophenyl)-diphenylphosphine, di-(sulfophenyl)phenylphosphine and tri(sulfophenylphosphine) accumulates in the sulfonation of triphenylphosphine, such as is known, for example, in DE-OS 2627 354. In prior art (sulfophenyl)-diphenylphosphine is abbreviated as TPPMS, di-(sulfophenyl)phenylphosphine as TPPDS and tri(sulfophenyl)phosphine as TPPTS.

As sulfonated arylphosphines are also suitable sulfonated disphosphines having the general formula (11) or (12)

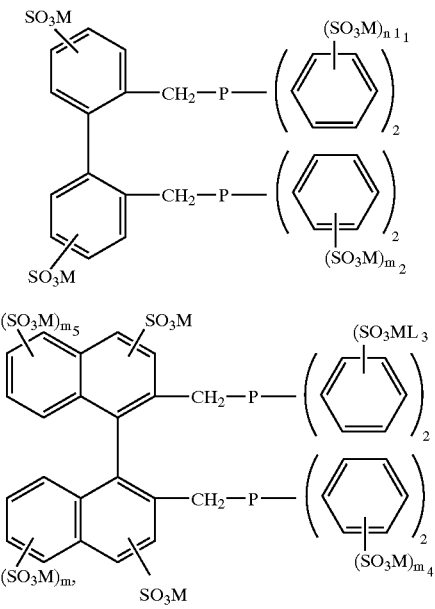

These phosphines of general formulas (11) and (12) are known from WO 98/30526.

In (11) each $m_2$ and $m_2$ represent independently of one another 0 or 1, and the compound of formula (11) contains up to six —$SO_3M$ groups.

In (12) each $m_3$, $m_4$, $m_5$ and $m_6$ represent independently of one another 0 or 1, and the compound of formula (12) contains four to eight —$SO_3M$ groups.

Due to the production by sulfonation of the corresponding diphosphines of formulas (11a) and (12a), which do not contain any —$SO_3M$ groups,

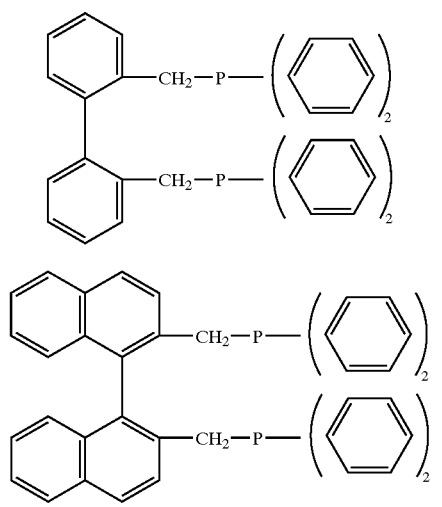

mixtures of compounds (11) and (12) with differing numbers of —$SO_3M$ groups are conventionally obtained. A compound of formulas (11) or (12), which contains for example three —$SO_3M$ groups, also contains compounds with only two —$SO_3M$ groups but also compounds with four or five —$SO_3M$ groups. A compound of formulas (11) or (12) with, for example, five —$SO_3M$ groups conventionally contains also compounds with only three or four —$SO_3M$ groups but also compounds with six or seven —$SO_3M$ groups.

Compounds of formula (11) have a maximum of six —$SO_3M$ groups, while compounds of formula (12) have a maximum of eight —$SO_3M$ groups.

For this reason, as a rule mixtures of compounds of formula (11) and (12) with differing numbers of —$SO_3M$ m groups are employed.

In formulas (11) and (12) M represents ammonium, a monovalent metal or the equivalent of a multivalent metal, in particular sodium, potassium, calcium or barium.

As sulfonated arylphosphines are suitable especially sulfonated diphosphines, which can be derived from the xanthene backbone having the general formula (13)

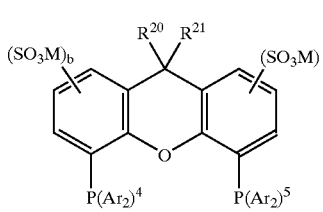

in which $R^{20}$ and $R^{21}$ are identical or different and represent a linear or branched alkyl radical with 1 to 6 carbon atoms or an aralkyl radical with 7 to 14 carbon atoms, a and b are identical or different and represent 1, 2 or 3, M represents ammonium, a monovalent metal or the equivalent of a multivalent metal, in particular sodium, potassium, calcium or barium and $Ar^4$ and $Ar^5$ represent identical or different aryl groups with 6 to 14 carbon atoms.

Such diphosphines of general formula (13) are preferably used in which $Ar^4$ and $Ar^5$ represent phenyl, a and b equal 1 and the $SO_3M$ group is in the 2,8 position, i.e. in the meta position with respect to the phosphorus atom.

The phosphines based on the xanthene skeleton are known from Organometallics 2000, Vol. 19, pp. 872–883, from which the sulfonated arylphosphines of general formula 13 are obtained by sulfonation.

The rhodium concentration in the ionic liquid is 10 to 1000 ppm by weight, preferably 50 to 500 ppm by weight, each relative to the ionic liquid. Although it is possible to employ as a catalyst the stoichiometrically composed rhodium-phosphorus complex, work usually takes place in the presence of excess phosphorus ligand, i.e. a ligand, which has not formed a complex bond with rhodium. The rhodium-phosphorus complex together with the excess ligand is also referred to as catalyst system. For each mole of rhodium, preferably 2 to 1000 moles of phosphorus in the form of the organic phosphorus (III) compounds are employed. Molar ratios of rhodium to phosphorus in the range of 1:5 to 1:100 have been found especially useful. The rhodium-phosphorus complex catalyst does hot need to be composed uniformly, but rather can comprise, for example, a mixture of rhodium complex, which differ in the type of phosphorus compounds.

The free phosphorus ligand contained in the ionic liquid can also be composed of a mixture of different organic phosphorus (III) compounds.

The second component of the catalyst system, namely the rhodium, can be employed either as the metal in finely distributed form, preferably on a support material such as activated charcoal, calcium carbonate, alumina or similar substrates, or as the rhodium compound. Examples of inorganic or organic rhodium compounds, in which the rhodium can be present in its various oxidation states, are the rhodium oxides $Rh_2O$, $Rh_2O_3$, $RhO_2$, $RhO_3$, the salts of the inorganic hydrogen acid such as halogenides, sulfides, selenides and tellurides, the salts of inorganic oxygen acids such as rhodium nitrate, rhodium sulfate, rhodium perchlorate, as well as the salts of aliphatic mono- or polycarboxylic acids, such as rhodium acetate, rhodium propionate, rhodium oxalate, rhodium malonate and rhodium-2-ethylhexanoate. Furthermore, carbonyl compounds of rhodium such as tricarbonyl rhodium, $Rh(CO)_3$, tetracarbonyl rhodium, $[Rh(CO)_4]_2$, tetrarhodium dodekacarbonyl, $Rh_4(CO)_{12}$, and rhodium acetylacetonatedicarbonyl $[Rh(acac)(CO)_2]$ have been found highly useful. While halogen carbonyl compounds such as dicarbonyl rhodium bromide, --■--■-- —[Rh $(CO)_2]Br$, and dicarbonyl rhodium iodide, $[Rh(CO)_2]I$, can also be employed, due to the corrosive behavior of halogen ions, they have only limited application. Lastly, complexes of rhodium, especially rhodium (III) compounds, are also suitable starting materials for the production of the catalytically active metal component of the catalyst system. These compounds contain mono-, bi- or tridentate ligands such as {3-diketones, for example acetylacetone, further alkylamines, alkyl or aryldiamines, nitrogen-containing heterocyclic compounds such as pyridine, or aliphatic or cycloaliphatic and diethylenically unsaturated hydrocarbons such as cyclopentadiene and 1,5-cyclooctadiene. Rhodium compounds especially suitable for the formation of the catalyst system are rhodium oxides, rhodium carbonyls, rhodium acetate, rhodium-2-ethylhexanoate and rhodium (III)-acetylacetonate.

The catalyst system can be produced in the initial stage of the conversion in situ, i.e. in the reaction phase, under reaction conditions and in the presence of the olefin, from the component rhodium or rhodium compound, organic phosphorus compound and synthesis gas. It is also possible, however, to preform the catalyst system separately from the hydroformylation step in a separate reaction step and subsequently to add it to the reaction mixture. For the preforming, metallic rhodium or a rhodium compound and organic phosphorus compound are suspended or dissolved in the ionic liquid and the mixture is treated with synthesis gas. Typical reaction conditions are temperatures of 90 to 150° C., in particular 100 to 120° C. and pressures of 0.2 to 10, preferably 0.5 to 5, MPa. The reaction time is up to 5 hours, depending on the reaction conditions selected.

The conversion of the olefins or the olefinically unsaturated compounds with hydrogen and carbon monoxide to carbonyl compounds takes place at temperatures of 20 to 150° C., preferably 80 to 140° C. and in particular 100 to 125° C., and pressures of 0.1 to 20 MPa, preferably 0.5 to 12 MPa and especially 1 to 7 MPa. The reaction conditions to be applied in"the;"indiyidual_case_depend also on the type of the olefinic compound to be converted. Reactive chemicals can already be converted at relatively low temperatures and pressures and in the presence of small quantities of catalyst, while chemically inert compounds require correspondingly more vigorous reaction conditions.

The composition of the synthesis gas, i.e. the proportions of carbon monoxide and hydrogen in the gas mixture, can be varied within a broad range. In general, mixtures are used, in which the ratio of volumes of carbon monoxide to hydrogen is 5:1 to 1:5. This ratio is conventionally 1:1 or deviates only slightly from this value.

The olefinic compound can be supplied as such or in solution to the hydroformylation reaction. Suitable solvents are ketones such as acetone, methylethylketone, acetophenone, dialkylethers, such as di-n-butylether, lower aliphatic nitriles such as acetonitrile, propionitrile or benzonitrile, dimethylformamide, linear or branched saturated aliphatic monohydroxy compounds such as methanol, ethanol, propanol and isopropanol, aromatic hydrocarbons such as benzene or toluene and saturated cycloaliphatic hydrocarbons such as cyclopentane or cyclohexane or saturated aliphatic hydrocarbons.

The process according to the invention can be carried out in stages as well as also continuously. After termination of the conversion, two phases are obtained, specifically with the lighter reaction products as the upper and specifically with the heavier catalyst solution as the lower phase. Both substance mixtures can be ■separated in simple manner, for example, by decanting.

To facilitate and complete the phase separation, it may be appropriate to add a nonpolar organic solvent. As organic nonpolar solvents are suitable aliphatic, cycloaliphatic or aromatic hydrocarbons, in particular pentane, hexane, cyclohexane, heptane, octane, i-octane, decane, dodecane, toluene, xylene, mesitylene or: ethylbenzene. After phase separation, the catalyst system can be completely or partially returned to the hydroformylation process. The separated organic phase is separated by distillation into its component solvent and crude aldehyde, after which the solvent can be returned to the phase separation process and the crude aldehyde is subjected to further purification processes or to a subsequent conversion.

Application of the novel method is not limited to specific olefins as starting materials. Accordingly, aliphatic, cycloaliphatic compounds or compounds with an alkylaryl radical, which have one or more olefinic double bonds, and, possibly also functional groups, can be converted. Examples of aliphatic compounds are linear or branched olefins with terminal or. internal double bonds such as ethylene, propylene, 1-butene, 2-butene, isobutene, 1-pentene, 2-methyl-1-butene, 1-hexene, 1-heptene, 1-octene, 2-octene, 3-octene, 2,4,4-trimethyl-1-pentene, 1-nonene, 2-propyl-1-hexene, 1-decene, 3-decene, 3-undecene, 4,4-methyl-1-nonene, 6-propyl-1-decene. Conjugated polyolefins, such as, for example, 1,3-butadiene, can be successfully converted. As cycloaliphatic reagents can be considered, for example, dicyclopentadiene, vinylcyclohexene, cyclooctadiene and cyclic terpenes, such as limonenes and pinenes. Examples of olefins with an alkylaryl radical are styrene, a-methylstyrene, 1,1-diphenylethylene, divinylbenzene and m-hexylstyrene.

Examples of olefinic compounds with functional groups are alcohols, aldehydes, carboxylic acids, esters, nitriles and halogen compounds. Among them are vinyl compounds, especially ethers and esters such as vinylmethylether, vinylethylether, P~naphthaline, o-vinyl-p-xylene, vinyl acetate; allyl compounds, among them especially the alcohols and esters such as allyl alcohol, allylethylether and allyl acetate; aldehydes such as acrolein, methacrolein, crotonaldehyde; esters of acrylic acid, methacrylic acid, fumade acid and maleic acid; acrylonitrile. This list of suitable starting materials is not exhaustive but is only given as examples.

The process according to the invention is especially suitable for hydroformylation of-water-sensitive olefins and olefin derivatives, such as esters of vinyl alcohol, for example vinyl acetate, vinyl propionate, of allyl alcohol, such as allyl acetate, allyl propionate, allyl butyrate, esters of acrylic acid and acetates of acrolein. Especially successful is the hydroformylation according to the new method of olefins and olefin derivatives with 2 to 20 carbon atoms.

The following examples will explain the invention, but not limit it.

EXAMPLES

1. Hydfoformylation of 1-octene in BEIM-Tos

A catalyst solution containing 5.3 mg Rh(acac)(CO)$_2$ and 40.0 mg 4,6-bis(diphenylphosphino)-9,9'-dimethyl-2,8-disodiumdisulfonatoxanthene in 5 mL of 1-butyl-3-ethylimidazolium-tosylate (BEIM-Tos) and 0.87 g dibutylether as internal standard was preformed for 0.5 h at 120° C. with synthesis gas (CO/H$_2$=1:1) at a total pressure of 1.1 MPa in the autoclave. After the preforming, 2.24 g 1-octene were added and hydroformylated for 2 h at 1.1 MPa. The reactor content was cooled to ambient temperature, removed and the phases separated. The organic phase was analyzed by gas chromatography and the rhodium content determined by ICP measurements (ICP—Inductive Coupled Plasma).

Conversion: 56%, n/i=33:1, TOF=270 h$^{-1}$ (turnover frequency), sum of hydration and isomerization products: 8.4%, [RhJ=0.060 ppm (rhodium concentration in the separated organic phase).

2. Hydroformylation of 1-octene in BMIM-OcSO$_4$

A catalyst solution containing 5.1 mg Rh(acac)(CO)$_2$ and 38.5 mg 4,6-bis(diphenylphosphino)-9,9'-dimethyl-2,8-disodiumdisulfonatoxanthene in 5 mL 1-butyl-3-methylimidazolium-octylsulfate (BMIM-OcSo$_4$) and 0.84 g dibutylether as internal standard was preformed in the autoclave for 0.5 h at 120° C. with synthesis gas (CO/H$_2$=1:1) at a total pressure of 1.1 MPa. After the preforming, 2.28 g 1-octene were added and hydroformylated for 2 h at 1.1 MPa. The reactor content was cooled to ambient temperature, removed and 6 mL cyclohexane were added for the phase separation. The organic phase was analyzed by gas chromatography and the rhodium content was determined by ICP measurements.

Conversion: 63%, n/i=49:1, TOF=323 h$^{-1}$, sum of hydration and isomerization products: 10.0%, [Rh]=0.368 ppm.

Comparison Example

Hydroformylation of 1-octene in BMIM-PF$_6$

A catalyst solution containing 5.1 mg Rh(acac)(CO)$_2$ and 38.1 mg 4,6-bis(diphenylphosphino)-9,9'-dimethyl-2,8-disodiumdisulfonatoxanthene in 5 mL 1-butyl-3-methylimidazolium-hexafluorophosphate (BMIM-PF$_6$) and 0.86 g dibutylether as internal standard was preformed in the autoclave for 0.5 h at 120° C. with synthesis gas (CO/H$_2$=1:1) at a total pressure of 1.1 MPa. After the preforming, 2.37 g 1-octene were added and hydroformylated for 2 h at 1.1 MPa. The reactor content was cooled to ambient temperature, removed and the phases were separated. The organic phase was analyzed by gas chromatography and the rhodium content was determined by ICP measurements.

Conversion: 17%, n/i=33.1, TOF=85 h$^{-1}$, sum of hydration and isomerization products: 3.0%, [Rh]=0.027 ppm.

As the results of the examples according to the invention show, markedly higher conversion, selectivity and TOF values can be observed in the hydroformylation reaction, if, instead of the known ionic liquids based on complex halogen-containing anions, such ionic liquids are employed which have organic sulfonates or sulfates as anions. The rhodium transfer from the ionic liquid into the organic phase is also low.

The invention claimed is:

1. A method for the production of aldehydes comprising reacting a member selected from the group consisting of mono-olefins, conjugated and nonconjugated polyolefins, cycloolefins and derivatives thereof, with carbon monoxide and hydrogen at a temperature of 20 to 150° C. and a pressure of 0.1 to 20 MPa in the presence of a nonaqueous ionic liquid of the formula $(Q^\oplus)_a A^{a-}$ and at least one rhodium compound and at least one sulfonated arylphosphine, wherein $Q^\oplus$ is a singly charged ammonium cation, which may be substituted by organic groups, or the equivalent of a multiply charged ammonium cation, which may be substituted by organic groups, and $A^{a-}$ is an organic sulfonate or organic sulfate of the formula

  (1)

wherein $R^1$ and $R^2$ are independently selected from the group consisting of alkyl of 1 to 20 carbon atoms, alkylaryl of 7 to 20 carbon atoms, an aryl of 6 to 14 carbon atoms, cycloalkyl of 3 to 7 carbon atoms and aralkyl of 7 to 20 carbon atoms; or $R^1$ has the formula

  (1a)

wherein $R^3$ is selected from the group consisting of alkyl of 1 to 20 carbon atoms, alkylaryl of 7 to 20 carbon atoms, aryl of 6 to 14 carbon atoms, cycloalkyl of 3 to 7 carbon atoms and aralkyl of 7 to 20 carbon atoms, n is an integer from 2–12 and m is an integer 1–100; and a is an integer and represents the number of the sulfones or sulfates bound to the organic radical and is at least equal to 1.

2. The method of claim 1, wherein $R^1$ and $R^2$ are independently selected from the group consisting of alkyl of 1 to 12 carbon atoms, alkylaryl of 7 to 12 carbon atoms, aryl of 6–10 carbon atoms, cycloalkyl of 5 to 7 carbon atoms and aralkyl of 7 to 12 carbon atoms, $R^3$ is selected from the group consisting of alkyl of 1 to 12 carbon atoms, alkylaryl with of 7 to 12 carbon atoms, aryl of 6 to 10 carbon atoms, cycloalkyl of 5 to 7 carbon atoms and aralkyl of 7 to 12 carbon atoms, n is 2, 3 or 4, m is an integer between 1 to 50 and a is 1 or 2.

3. The method of claim 1 wherein the organic sulfonate is tosylate and the organic sulfate is octylsulfate.

4. The method of claim 1 wherein $Q^\oplus$ are ammonium ions of the formulas

  (2)

  (3)

wherein $R^4$, $R^5$m $R^6$ and $R^7$ are individually selected from the group consisting of hydrogen aliphatic hydrocarbon of 1 to 20 carbon atoms, cycloaliphatic and aromatic hydrocarbon of 6 to 20 carbon atoms and alkoxy of 1 to 10 carbon atoms with the provision that at least one $R^4$, $R^5$, $R^6$, $R^7$ is not hydrogen.

5. The method of claim 1 wherein $Q^\oplus$ is selected from the group consisting of saturated or unsaturated cyclic and aromatic each with a tridentate nitrogen atom in a 4 to 10-membered heterocyclic ring having the formulas

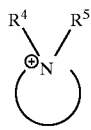

(4)

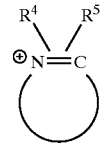

(5)

where $R^4$ and $R^5$ are individually selected from the group consisting of hydrogen aliphatic hydrocarbon of 1 to 20 carbon atoms, cycloaliphatic and aromatic hydrocarbon of 6 to 20 carbon atoms and alkoxy of 1 to 10 carbon atoms.

6. The method of claim 1 wherein $Q^⊕$ is quaternary ammonium ions of the formulas $$R^4R^5R^6N^⊕\text{-}G\text{-}N^⊕R^7R^8R^9 \quad (6)$$

$$R^4R^5N^⊕=CR^6\text{-}G\text{-}R^6C=N^⊕R^4R^5 \quad (7)$$

wherein $R^4$, $R^5$, $R^6$, $R^7$, $R^8$ and $R^9$ are individually selected from the group consisting of hydrogen, aliphatic hydrocarbon of 1 to 20 carbon atoms, cycloaliphatic and aromatic hydrocarbon of 6 to 30 carbon atoms, alkylaryl and aralkyl of 7 to 40 carbon atoms and alkoxy of 1 to 10 carbon atoms; G is $(-CH^{10-})_d$, where $R^{10}$ is hydrogen or hydrocarbon of 1 to 5 carbon atoms and d is an integer from 1 to 8, or arylene of 6 to 30 carbon atoms or alkylenearyl of 7 to 40 carbon atoms.

7. The method of claim 1 wherein $Q^⊕$ is imidazolium ions of the formula

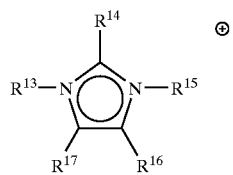

(9)

wherein $R^{13}$, $R^{14}$, $R^{15}$, $R^{16}$ and $R^{17}$ are individually selected from the group consisting of hydrogen, of 1 to 30 carbon atoms, aryl of 6 to 40 carbon atoms, alkylaryl of 7 to 40 carbon atoms and $-SiR_3^{18}$ wherein $R^{18}$ is alkyl of 1 to 30 carbon atoms or aryl of 6 to 40 carbon atoms.

8. The method of claim 7, wherein $Q^⊕$ is selected from the group consisting of
ethyl-3-methyl-2,4,5-H-imidazolium, 1-propyl-3-methyl-2,4,5-H-imidazolium, 1-butyl-3-methyl-2,4,5-H-imidazolium, 1-butyl-3-ethyl-2,4,5-H-imidazolium, 1,3,4,5-tetramethyl-2-H-imidazolium, 2,4,5-trimethyl-1,3-H-imidazolium, 1,2,3,4,5-pentamethylimidazolium, 1,2,3,5-tetramethyl-4-H-imidazolium, 1,2,3,4-tetramethyl-5-H-imidazolium, 1,3,4,5,-tetraphenyl-2-H-imidazolium, 1,3-dimethyl-4,5-diphenyl-2-H-imidazolium, 1-ethyl-3-isopropyl-2,4,5-H-imidazolium, 1-butyl-3-octanyl-2,4,5-H-imidazolium, 1-propyl-3-octanyl-2,4,5-H-imidazolium, 1-ethyl-3-octanyl-2,4,5-H-imidazolium, 1-methyl-3-octanyl-2,4,5-H-imidazolium, 1,3-diisopropyl-4,5-dimethyl-2-H-imidazolium, 1,4,5-trimethyl-3-trimethylsilyl-2-H-imidazolium, 2-ethyl-4-methyl-1,3,5-H-imidazolium, 1,3-adamantyl-4,5-dimethyl-1-H-imidazolium, 1,2,4,5-tetramethyl-3-H-imidazolium, 1-methyl-2,3,4,5-H-imidazolium, 1,3-dimethyl-2,4,5-H-imidazolium, 2-methyl-4,5,-ethyl-1,3-H-imidazolium, 2,4,5-trimethyl-1,3-H-imidazolium, 1-ethyl-2,3,4,5-H-imidazolium, 1,3-diethyl-4,5-dimethyl-2-H-imidazolium, 1,3-diphenyl-4,5-dimethyl-2-H-imidazolium, 1,3-diphenyl-2,4,5-H-imidazolium, 1,3-dimethoxy-4,5-dimethyl-2-H-imidazolium, 1-trimethylsilyl-2,3,5-trimethyl-4-H-imidazolium.

9. The method of claim 1 wherein the sulfonated arylphosphine is a sulfonated triarylphosphine of the formula

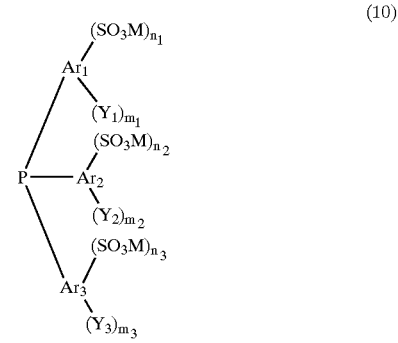

(10)

wherein $Ar^1$, $Ar^2$ and $Ar^3$ are individually aryl of 6 to 14 carbon atoms, $Y_1$, $Y_2$ and $Y_3$ are individually selected from the group consisting of alkyl and alkoxy of 1 to 4 carbon atoms, chlorine, bromine, hydroxyl, cyanide, nitro and $NR^{18}R^{19}$, $R^{18}$ and $R^{19}$ are individually hydrogen, or alkyl of 1 to 4 carbon atoms, M is selected from the group consisting of lithium, sodium, potassium, magnesium, calcium and barium, $m_1$, $m_2$ and $m_3$ are individually integers from 0 to 5, $n_1$, $n_2$ and $n_3$ are individually integers from 0 to 3, and at least one of $n_1$, $n_2$ and $n_3$ is equal to or greater than 1.

10. The method of claim 1 wherein the sulfonated arylphosphine is a sulfonated diarylphosphine of the formula

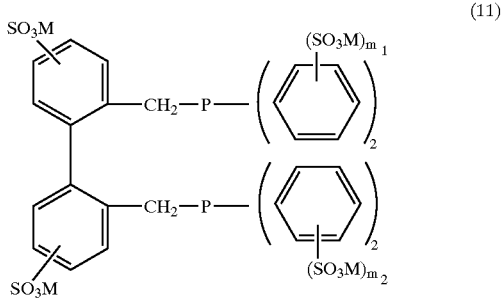

(11)

wherein $m_1$ and $m_2$, are independently 0 or 1, the compound of formula (11) contains up to six —$SO_3M$ groups and M is selected from the group consisting of ammonium, a monovalent metal and the equivalent of a multivalent metal.

11. The method of claim 1 wherein the sulfonated arylphosphine is a sulfonated diarylphosphine of formula

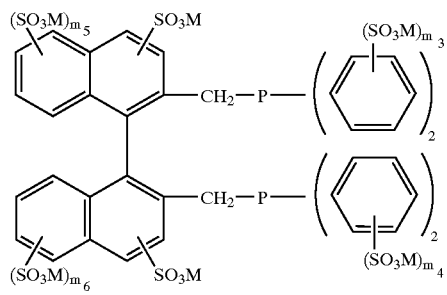

(12)

wherein $m_3$, $m_4$, $m_5$ and $m_6$ are independently 0 or 1, the compound of formula (12) contains four to eight —$SO_3M$ groups, and M is selected from the group consisting of ammonium, a monovalent metal and the equivalent of a multivalent metal.

12. The method of claim 1 wherein the sulfonated arylphosphine is a sulfonated diarylphosphine of the formula

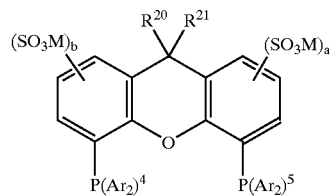

(13)

wherein $R^{20}$ and $R^{21}$ are individually alkyl of 1 to 6 carbon atoms or aralkyl of 7 to 14 carbon atoms, a and b are individually 1, 2 or 3, M is selected from the group consisting of ammonium, a monovalent metal and the equivalent of a multivalent metal, and $Ar^4$ and $Ar^5$ are individually aryl of 6 to 14 carbon atoms.

13. The method of claim 1 wherein for each mole of rhodium 2 to 1000 moles of phosphorus(III) are used.

14. The method of claim 1 wherein the rhodium concentration is 10 to 1000 ppm by weight, with respect to the ionic liquid.

15. The method of claim 1 wherein the reaction is carried out at 80 to 140° C.

16. The method of claim 1 wherein the reaction is carried out at pressures of 0.5 to 12 Mpa.

17. The method of claim 1 wherein olefins or olefin derivatives of 2 to 20 carbon atoms are used.

18. The method of claim 1 wherein the organic aldehyde-containing phase and the rhodium-containing ionic liquid are separated from one another by phase separation and the separated rhodium-containing ionic liquid is recycled completely or partially to the hydroformylation reaction vessel.

19. The method of claim 18, wherein, during the phase separations a nonpolar organic solvent is added.

\* \* \* \* \*